United States Patent
Karashima et al.

(10) Patent No.: US 10,226,426 B2
(45) Date of Patent: Mar. 12, 2019

(54) SUSPENSION CONTAINING NANO-COCRYSTAL AND MANUFACTURING METHOD

(71) Applicant: TAKEDA PHARMACEUTICAL COMPANY LIMITED, Osaka (JP)

(72) Inventors: Masatoshi Karashima, Kanagawa (JP); Katsuhiko Yamamoto, Kanagawa (JP); Takashi Kojima, Kanagawa (JP); Yukihiro Ikeda, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/554,688

(22) PCT Filed: Mar. 1, 2016

(86) PCT No.: PCT/JP2016/056236
§ 371 (c)(1),
(2) Date: Aug. 30, 2017

(87) PCT Pub. No.: WO2016/140219
PCT Pub. Date: Sep. 9, 2016

(65) Prior Publication Data
US 2018/0036244 A1  Feb. 8, 2018

(30) Foreign Application Priority Data
Mar. 2, 2015 (JP) .................. 2015-040647

(51) Int. Cl.
*A61K 9/14* (2006.01)
*A61K 47/16* (2006.01)
(Continued)

(52) U.S. Cl.
CPC .............. *A61K 9/146* (2013.01); *A61K 9/10* (2013.01); *A61K 9/145* (2013.01); *A61K 9/1617* (2013.01);
(Continued)

(58) Field of Classification Search
CPC .......... A61K 9/146; A61K 9/10; A61K 47/38
See application file for complete search history.

(56) References Cited

U.S. PATENT DOCUMENTS

2006/0068059 A1  3/2006  Boghani et al.
2006/0276483 A1  12/2006  Surber et al.
(Continued)

FOREIGN PATENT DOCUMENTS

JP  2008-503495  2/2008
JP  2008-514241  5/2008
(Continued)

OTHER PUBLICATIONS

De Smet, et al., "Formulation of itraconazole nanococrystals and evaluation of their bioavailability in dogs", European Journal of Pharmaceutics and Biopharmaceutics 87 (2014) 107-113.
(Continued)

*Primary Examiner* — Carlos A Azpuru
(74) *Attorney, Agent, or Firm* — Anne M. Reynolds; Casimir Jones, S.C.

(57) ABSTRACT

The present invention provides a method of producing a suspension containing a nano-cocrystal having an average particle size of not more than 300 nm, a polymer having a number average molecular weight of not less than 3,000, a surfactant having a number average molecular weight of less than 3,000 and water, which method including wet grinding a cocrystal, which is constituted of an organic compound and a cocrystal former and is not dissociated by wet grinding, in water containing the polymer and the surfactant.

4 Claims, 8 Drawing Sheets

(51) Int. Cl.

| | |
|---|---|
| A61K 47/18 | (2017.01) |
| A61K 47/20 | (2006.01) |
| A61K 47/22 | (2006.01) |
| A61K 47/32 | (2006.01) |
| A61K 47/34 | (2017.01) |
| A61K 9/10 | (2006.01) |
| A61K 47/38 | (2006.01) |
| A61K 31/341 | (2006.01) |
| A61K 31/405 | (2006.01) |
| A61K 31/55 | (2006.01) |
| A61K 31/522 | (2006.01) |
| A61K 9/16 | (2006.01) |

(52) U.S. Cl.
CPC .......... *A61K 9/1623* (2013.01); *A61K 9/1652* (2013.01); *A61K 31/341* (2013.01); *A61K 31/405* (2013.01); *A61K 31/522* (2013.01); *A61K 31/55* (2013.01); *A61K 47/16* (2013.01); *A61K 47/18* (2013.01); *A61K 47/20* (2013.01); *A61K 47/22* (2013.01); *A61K 47/32* (2013.01); *A61K 47/34* (2013.01); *A61K 47/38* (2013.01)

(56) References Cited

U.S. PATENT DOCUMENTS

| | | | |
|---|---|---|---|
| 2007/0299033 | A1 | 12/2007 | McMahon et al. |
| 2010/0184792 | A1 | 7/2010 | Sowa et al. |
| 2011/0177136 | A1 | 7/2011 | Paradkar et al. |
| 2011/0236478 | A1 | 9/2011 | Dokou et al. |
| 2012/0028998 | A1 | 2/2012 | Sansone et al. |
| 2012/0039957 | A1* | 2/2012 | Brzeczko ............ A61K 9/2054 424/400 |
| 2012/0128740 | A1 | 5/2012 | Filipcsei et al. |
| 2014/0255498 | A1 | 9/2014 | Remon et al. |
| 2016/0309718 | A1 | 10/2016 | Yamamura |

FOREIGN PATENT DOCUMENTS

| | | |
|---|---|---|
| JP | 2008-540676 | 11/2008 |
| JP | 2010-538037 | 12/2010 |
| JP | 2011-529101 | 12/2011 |
| JP | 2012-501971 | 1/2012 |
| JP | 2012-522026 | 9/2012 |
| JP | 2012-530125 | 11/2012 |
| WO | WO 2011/154755 | 12/2011 |
| WO | WO 2013/057169 | 4/2013 |
| WO | WO 2013/147072 | 10/2013 |
| WO | WO 2015/093367 | 6/2015 |

OTHER PUBLICATIONS

Goud, N.R., et al., "Novel Furosemide Cocrystals and Selection of High Solubility Drug Forms", J. Pharm. Sci., vol. 101, No. 2, 2012, 664-680.

Karashima, et al., "A novel solubilization technique for poorly soluble drugs through the integration of nanocrystal and cocrystal technologies", European Journal of Pharmaceutics and Biopharmaceutics 107 (2016) 142-150.

Kojima, T., et al., "High-throughput cocrystal slurry screening by use of in situ Raman microscopy and multi-well plate", Int. J. Pharm., 399, 2010. 52-59.

Poster presented on May 21, 2015 in the 30th Annual Meeting of the Academy of Pharmaceutical Science and Technology, Japan (with English translation).

Sander, et al., "Pharmaceutical Nano-Cocrystals: Sonochemical Synthesis by Solvent Selection and Use of a Surfactant", Angew. Chem. Int. Ed. 2010, 49, 7284-7288.

Supplementary European Search Report dated Oct. 15, 2018, European Application No. 16758912.6, 3 pages.

Kesisglou, et al., "Nanosizing—oral formulation development and biopharmaceutical evaluation." Adv Drug Deliv Rev. Jul. 30, 2007;59(7):631-44.

\* cited by examiner

SUSPENSION CONTAINING NANO-COCRYSTAL AND MANUFACTURING METHOD

CROSS-REFERENCE TO RELATED APPLICATION(S)

This is a U.S. national stage entry of International Patent Application No. PCT/JP2016/056236, filed on Mar. 1, 2016, which claims priority to Japanese Patent Application No. 2015-040647, filed on Mar. 2, 2015, the entire contents of all of which are fully incorporated herein by reference.

TECHNICAL FIELD

The present invention relates to a suspension or composition containing a nano-cocrystal and a production method of these.

BACKGROUND OF THE INVENTION

It is important for the development of pharmaceutical products to improve dissolution property of poorly soluble drugs. As a technique for improving dissolution property of poorly soluble drugs, pulverization of a poorly soluble drug by a precipitation method, wet grinding and the like, and formation of a salt or cocrystal of a poorly soluble drug are known (patent documents 1-4 and non-patent documents 1-4). As used herein, the "cocrystal" generally means a crystal in which multicomponents constituting the cocrystal are linked by a bond or an interaction other than an ionic bond.

DOCUMENT LIST

Patent Documents patent document 1: WO 2013/057169
patent document 2: WO 2011/154755
patent document 3: JP-A-2012-530125
patent document 4: JP-A-2008-540676

Non-Patent Documents non-patent document 1: Lieselotte De Smet, et al., "Formulation of itraconazole nanococrystals and evaluation of their bioavailability in dogs", European Journal of Pharmaceutics and Biopharmaceutics 87 (2014) 107-113
non-patent document 2: John R. G. Sander, et al., "Pharmaceutical Nano-Cocrystals: Sonochemical Synthesis by Solvent Selection and Use of a Surfactant", Angew. Chem. Int. Ed. 2010, 49, 7284-7288
non-patent document 3: Goud, N. R., et al., "Novel Furosemide Cocrystals and Selection of High Solubility Drug Forms", J. Pharm. Sci., Vol. 101, No. 2, 2012, 664-680
non-patent document 4: Kojima, T., et al., "High-throughput cocrystal slurry screening by use of in situ Raman microscopy and multi-well plate", Int. J. Pharm., 399, 2010. 52-59

SUMMARY OF THE INVENTION

Problems to be Solved by the Invention

The aforementioned prior art (pulverization or cocrystallization) is sometimes insufficient for the improvement of the dissolution property of an organic compound (particularly, a poorly soluble drug). The present invention has been made by taking note of such situation, and an object thereof is to improve dissolution property of an organic compound compared to the prior art.

Means of Solving the Problems

The present inventors have conducted intensive studies in an attempt to achieve the above-mentioned object, and found that a fine nano-cocrystal constituted of an organic compound and a cocrystal former and superior in the dissolution property can be produced by using a polymer and a surfactant in combination in the wet grinding of the cocrystal. The present invention is based on this finding and provides the following.

[1] A method of producing a suspension comprising a nano-cocrystal having an average particle size of not more than 300 nm, a polymer having a weight average molecular weight of not less than 3,000, a surfactant having a weight average molecular weight of less than 3,000 and water, which method comprising wet grinding a cocrystal, which is constituted of an organic compound and a cocrystal former and is not dissociated by wet grinding, in water containing the polymer and the surfactant.

[2] The method of the aforementioned [1], wherein a ratio of water solubility (mg/mL) of the cocrystal former/water solubility (mg/mL) of the organic compound is less than $1.0 \times 10^5$.

[3] The method of the aforementioned [1], wherein a ratio of water solubility (mg/mL) of the cocrystal former/water solubility (mg/mL) of the organic compound is not more than $5.0 \times 10^4$.

[4] The method of the aforementioned [1], wherein a ratio of water solubility (mg/mL) of the cocrystal former/water solubility (mg/mL) of the organic compound is not more than $1.0 \times 10^4$.

[5] The method of any one of the aforementioned [1]-[4], wherein the polymer is at least one selected from the group consisting of hydroxypropylmethylcellulose, hydroxypropylcellulose, polyvinylpyrrolidone, poly(vinyl alcohol), polyethylene glycol, methacrylic acid copolymer and Poloxamer 407.

[6] The method of any one of the aforementioned [1]-[4], wherein the polymer is hydroxypropylmethylcellulose.

[7] The method of any one of the aforementioned [1]-[6], wherein the polymer has a weight average molecular weight of 3,000-1,000,000.

[8] The method of any one of the aforementioned [1]-[6], wherein the polymer has a weight average molecular weight of 3,000-200,000.

[9] The method of any one of the aforementioned [1]-[8], wherein the surfactant is at least one selected from the group consisting of sodium dodecyl sulfate, cetyltrimethylammonium bromide, polysorbate 80, and sodium dioctylsulfosuccinate.

[10] The method of any one of the aforementioned [1]-[8], wherein the surfactant is sodium dodecyl sulfate.

[11] The method of any one of the aforementioned [1]-[10], wherein the polymer has a concentration of 0.3-2.5% (w/v) in water.

[12] The method of any one of the aforementioned [1]-[10], wherein the polymer has a concentration of 0.3-2.0% (w/v) in water.

[13] The method of any one of the aforementioned [1]-[10], wherein the polymer has a concentration of 0.3-1.5% (w/v) in water.

[14] The method of any one of the aforementioned [1]-[13], wherein the surfactant has a concentration of 0.02-0.30% (w/v) in water.
[15] The method of any one of the aforementioned [1]-[13], wherein the surfactant has a concentration of 0.03-0.20% (w/v) in water.
[16] The method of any one of the aforementioned [1]-[13], wherein the surfactant has a concentration of 0.04-0.15% (w/v) in water.
[17] The method of any one of the aforementioned [1]-[10], wherein the polymer has a concentration of 0.3-2.5% (w/v) and the surfactant has a concentration of 0.02-0.30% (w/v), each in water.
[18] The method of any one of the aforementioned [1]-[10], wherein the polymer has a concentration of 0.3-2.0% (w/v) and the surfactant has a concentration of 0.03-0.20% (w/v), each in water.
[19] The method of any one of the aforementioned [1]-[10], wherein the polymer has a concentration of 0.3-1.5% (w/v) and the surfactant has a concentration of 0.04-0.15% (w/v), each in water.
[20] The method of any one of the aforementioned [1]-[19], wherein the nano-cocrystal has a concentration of 0.1-100% (w/v) in water.
[21] The method of any one of the aforementioned [1]-[19], wherein the nano-cocrystal has a concentration of 0.5-50% (w/v) in water.
[22] The method of any one of the aforementioned [1]-[19], wherein the nano-cocrystal has a concentration of 1.0-20% (w/v) in water.
[23] The method of any one of the aforementioned [1]-[22], wherein the organic compound is furosemide, carbamazepine or indomethacin.
[24] The method of any one of the aforementioned [1]-[23], wherein the cocrystal former is saccharin or caffeine.
[25] A suspension obtained by the method of any one of the aforementioned [1]-[24].
[26] A suspension comprising a nano-cocrystal constituted of an organic compound and a cocrystal former, and having an average particle size of not more than 300 nm, a polymer having a weight average molecular weight of not less than 3,000, a surfactant having a weight average molecular weight of less than 3,000 and water, wherein the aforementioned cocrystal is not dissociated by wet grinding.
[27] The suspension of the aforementioned [26], wherein a ratio of water solubility (mg/mL) of the cocrystal former/water solubility (mg/mL) of the organic compound is less than $1.0 \times 10^5$.
[28] The suspension of the aforementioned [26], wherein a ratio of water solubility (mg/mL) of the cocrystal former/water solubility (mg/mL) of the organic compound is not more than $5.0 \times 10^4$.
[29] The suspension of the aforementioned [26], wherein a ratio of water solubility (mg/mL) of the cocrystal former/water solubility (mg/mL) of the organic compound is not more than $1.0 \times 10^4$.
[30] The suspension of any one of the aforementioned [26]-[29], wherein the polymer is at least one selected from the group consisting of hydroxypropylmethylcellulose, hydroxypropylcellulose, polyvinylpyrrolidone, poly(vinyl alcohol), polyethylene glycol, methacrylic acid copolymer and Poloxamer 407.
[31] The suspension of any one of the aforementioned [26]-[29], wherein the polymer is hydroxypropylmethylcellulose.
[32] The suspension of any one of the aforementioned [26]-[31], wherein the polymer has a weight average molecular weight of 3,000-1,000,000.
[33] The suspension of any one of the aforementioned [26]-[31], wherein the polymer has a weight average molecular weight of 3,000-200,000.
[34] The suspension of any one of the aforementioned [26]-[33], wherein the surfactant is at least one selected from the group consisting of sodium dodecyl sulfate, cetyltrimethylammonium bromide, polysorbate 80, and sodium dioctylsulfosuccinate.
[35] The suspension of any one of the aforementioned [26]-[33], wherein the surfactant is sodium dodecyl sulfate.
[36] The suspension of any one of the aforementioned [26]-[35], wherein the polymer has a concentration of 0.3-2.5% (w/v).
[37] The suspension of any one of the aforementioned [26]-[35], wherein the polymer has a concentration of 0.3-2.0% (w/v).
[38] The suspension of any one of the aforementioned [26]-[35], wherein the polymer has a concentration of 0.3-1.5% (w/v).
[39] The suspension of any one of the aforementioned [26]-[38], wherein the surfactant has a concentration of 0.02-0.30% (w/v).
[40] The suspension of any one of the aforementioned [26]-[38], wherein the surfactant has a concentration of 0.03-0.20% (w/v).
[41] The suspension of any one of the aforementioned [26]-[38], wherein the surfactant has a concentration of 0.04-0.15% (w/v).
[42] The suspension of any one of the aforementioned [26]-[35], wherein the polymer has a concentration of 0.3-2.5% (w/v) and the surfactant has a concentration of 0.02-0.30% (w/v).
[43] The suspension of any one of the aforementioned [26]-[35], wherein the polymer has a concentration of 0.3-2.0% (w/v) and the surfactant has a concentration of 0.03-0.20% (w/v).
[44] The suspension of any one of the aforementioned [26]-[35], wherein the polymer has a concentration of 0.3-1.5% (w/v) and the surfactant has a concentration of 0.04-0.15% (w/v).
[45] The suspension of any one of the aforementioned [26]-[44], wherein the nano-cocrystal has a concentration of 0.1-100% (w/v).
[46] The suspension of any one of the aforementioned [26]-[44], wherein the nano-cocrystal has a concentration of 0.5-50% (w/v).
[47] The suspension of any one of the aforementioned [26]-[44], wherein the nano-cocrystal has a concentration of 1.0-20% (w/v).
[48] The suspension of any one of the aforementioned [26]-[47], wherein the organic compound is furosemide, carbamazepine or indomethacin.
[49] The suspension of any one of the aforementioned [26]-[48], wherein the cocrystal former is saccharin or caffeine.
[50] A method of producing a composition comprising a nano-cocrystal having an average particle size of not more than 300 nm, a polymer and a surfactant, which comprises drying the suspension obtained by the method of any one of the aforementioned [1]-[24].
[51] A composition obtained by the method of the aforementioned [50].

[52] The composition of the aforementioned [51], wherein an amount of the polymer is 1.5-250 parts by weight per 100 parts by weight of the nano-cocrystal.
[53] The composition of the aforementioned [51], wherein an amount of the polymer is 5-100 parts by weight per 100 parts by weight of the nano-cocrystal.
[54] The composition of any one of aforementioned [51]-[53], wherein an amount of the surfactant is 0.1-30 parts by weight per 100 parts by weight of the nano-cocrystal.
[55] The composition of any one of aforementioned [51]-[53], wherein an amount of the surfactant is 0.5-10 parts by weight per 100 parts by weight of the nano-cocrystal.
[56] A composition comprising a nano-cocrystal constituted of an organic compound and a cocrystal former, and having an average particle size of not more than 300 nm, a polymer having a weight average molecular weight of not less than 3,000, and a surfactant having a weight average molecular weight of less than 3,000, wherein the aforementioned cocrystal is not dissociated by wet grinding.
[57] The composition of the aforementioned [56], wherein a ratio of water solubility (mg/mL) of the cocrystal former/water solubility (mg/mL) of the organic compound is less than $1.0 \times 10^5$.
[58] The composition of the aforementioned [56], wherein a ratio of water solubility (mg/mL) of the cocrystal former/water solubility (mg/mL) of the organic compound is not more than $5.0 \times 10^4$.
[59] The composition of the aforementioned [56], wherein a ratio of water solubility (mg/mL) of the cocrystal former/water solubility (mg/mL) of the organic compound is not more than $1.0 \times 10^4$.
[60] The composition of any one of the aforementioned [56]-[59], wherein the polymer is at least one selected from the group consisting of hydroxypropylmethylcellulose, hydroxypropylcellulose, polyvinylpyrrolidone, poly(vinyl alcohol), polyethylene glycol, methacrylic acid copolymer and Poloxamer 407.
[61] The composition of any one of the aforementioned [56]-[59], wherein the polymer is hydroxypropylmethylcellulose.
[62] The composition of any one of the aforementioned [56]-[61], wherein the polymer has a weight average molecular weight of 3,000-1,000,000.
[63] The composition of any one of the aforementioned [56]-[61], wherein the polymer has a weight average molecular weight of 3,000-200,000.
[64] The composition of any one of the aforementioned [56]-[63], wherein the surfactant is at least one selected from the group consisting of sodium dodecyl sulfate, cetyltrimethylammonium bromide, polysorbate 80, and sodium dioctylsulfosuccinate.
[65] The composition of any one of the aforementioned [56]-[63], wherein the surfactant is sodium dodecyl sulfate.
[66] The composition of any one of the aforementioned [56]-[65], wherein an amount of the polymer is 1.5-250 parts by weight per 100 parts by weight of the nano-cocrystal.
[67] The composition of any one of the aforementioned [56]-[65], wherein an amount of the polymer is 5-100 parts by weight per 100 parts by weight of the nano-cocrystal.
[68] The composition of any one of the aforementioned [56]-[67], wherein an amount of the surfactant is 0.1-30 parts by weight per 100 parts by weight of the nano-cocrystal.
[69] The composition of any one of the aforementioned [56]-[67], wherein an amount of the surfactant is 0.5-10 parts by weight per 100 parts by weight of the nano-cocrystal.
[70] The composition of any one of the aforementioned [56]-[69], wherein the organic compound is furosemide, carbamazepine or indomethacin.
[71] The composition of any one of the aforementioned [56]-[70], wherein the cocrystal former is saccharin or caffeine.
[72] A medicament comprising the suspension of any one of the aforementioned [25]-[49] or the composition of any one of the aforementioned [51]-[71].

Effect of the Invention

According to the production method of the present invention, a suspension or a composition containing a nano-cocrystal superior in the dissolution property can be obtained.

BRIEF DESCRIPTION OF THE DRAWINGS

FIG. 2(B): (e) IMC before wet grinding, (f) nanoized IMC after wet grinding, (g) IMC-SAC cocrystal before wet grinding, (h) IMC-SAC nano-cocrystal after wet grinding). The abbreviations mean as described in the Examples.

FIG. 3(B): (e) a powder of IMC, (f) a suspension of nanoized IMC, (g) a powder of IMC-SAC cocrystal, (h) a suspension of IMC-SAC nano-cocrystal). The abbreviations mean as described in the Examples.

DETAILED DESCRIPTION OF THE INVENTION

Figure 1:
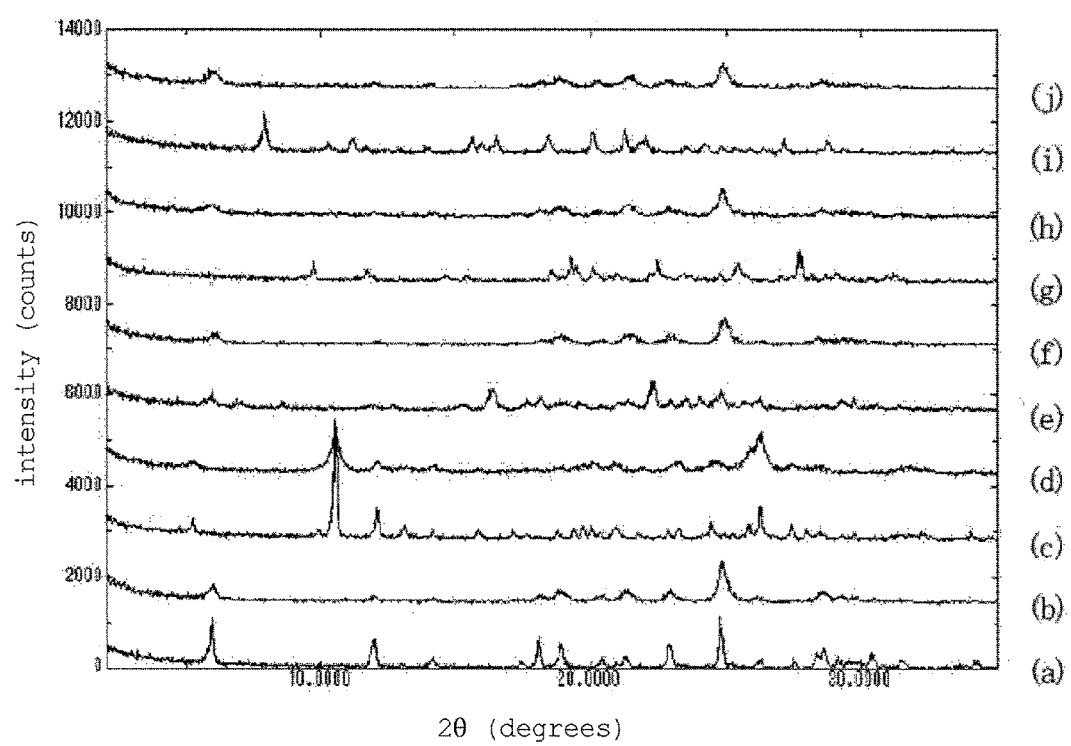
FIG. 1 shows X-ray diffraction patterns, obtained by powder X-ray diffractometry, of an organic compound and cocrystals before wet grinding, and X-ray diffraction patterns of a nanoized organic compound and nano-cocrystals after wet grinding ((a) FSD before wet grinding, (b) nanoized FSD after wet grinding, (c) FSD-CAF cocrystal before wet grinding, (d) FSD-CAF nano-cocrystal after wet grinding, (e) FSD-UREA cocrystal before wet grinding, (f) FSD-UREA after wet grinding (dissociation), (g) FSD-ACT cocrystal before wet grinding, (h) FSD-ACT after wet grinding (dissociation), (i) FSD-NIC cocrystal before wet grinding, (j) FSD-NIC after wet grinding (dissociation)). The abbreviations mean as described in the Examples.

The present invention provides a method of producing a suspension containing a nano-cocrystal having an average particle size of not more than 300 nm by wet grinding of a cocrystal not dissociated by wet grinding in water containing a polymer having a weight average molecular weight of not less than 3,000 (hereinafter sometimes to be simply referred to as a "polymer") and a surfactant having a weight average molecular weight of less than 3,000 (hereinafter sometimes to be simply referred to as a "surfactant"), and a suspension obtained by the method.

In the present invention, a "cocrystal" means a crystal in which an organic compound and a cocrystal former constituting the cocrystal are linked by a bond or an interaction other than an ionic bond (e.g., hydrogen bond, Van der Waals' force, π-π bond etc.). Whether a certain compound is a cocrystal or a salt in which the constituent components are linked by an ionic bond can be confirmed by a single-crystal X-ray diffraction method or solid-state NMR.

An organic compound and a cocrystal former constituting a cocrystal are preferably not salts. However, when an organic compound and a cocrystal former can be linked by a bond or an interaction other than an ionic bond to form a cocrystal, the organic compound may be a salt and the cocrystal former may be a salt.

A "nano-cocrystal" generally means a cocrystal having an average particle size of less than 500 nm. One of the characteristics of the production method of the present invention is production of a suspension containing a nano-cocrystal having an average particle size of not more than 300 nm. An average particle size of a nano-cocrystal is preferably not more than 250 nm, further preferably not more than 200 nm. The average particle size is a value measured by a dynamic scattering method.

One of the characteristics of the present invention is wet grinding of a cocrystal rather than an organic compound itself. When an organic compound itself is subjected to wet grinding, the organic compound is sometimes hydrated. Generally, hydrate shows lower water solubility as compared to anhydride. Hydration during wet grinding can be prevented by forming a cocrystal from an organic compound and a cocrystal former and then wet grinding the cocrystal. As shown in the following Table 12, absorbability can be improved by forming a cocrystal from an organic compound and a cocrystal former and then wet grinding the cocrystal, rather than simply wet grinding an organic compound.

One of the characteristics of the present invention is combined use of a polymer and a surfactant with wet grinding of a cocrystal. Wet grinding not using both a polymer and a surfactant and wet grinding of a cocrystal using only one of these cannot produce a suspension containing a nano-cocrystal having an average particle size of not more than 300 nm.

A weight average molecular weight of a polymer is preferably 3,000-1,000,000, more preferably 3,000-200,000. The weight average molecular weight is a value measured by gel permeation chromatography.

The polymer is preferably a water-soluble polymer m Examples of the water-soluble polymer include hydroxypropylmethylcellulose, hydroxypropylcellulose, polyvinylpyrrolidone, poly(vinyl alcohol), polyethylene glycol, methacrylic acid copolymer, Poloxamer 407 and the like. Examples of the methacrylic acid copolymer include a copolymer of methacrylic acid and methyl methacrylate, a copolymer of methacrylic acid and ethyl acrylate and the like. The amount of the unit of a monomer other than methacrylic acid in the methacrylic acid copolymer is preferably 0.5-4 mol, more preferably 1-3 mol, further preferably 1-2 mol, per 1 mol of methacrylic acid unit. Examples of the commercially available product of the methacrylic acid copolymer include Eudragit L100 (molar ratio of methacrylic acid unit:methyl methacrylate unit=1:1), Eudragit S100 (molar ratio of methacrylic acid unit:methyl methacrylate unit=1:2), Eudragit L30D-55 (molar ratio of methacrylic acid unit:ethyl acrylate unit=1:1), Eudragit L100-55 (molar ratio of methacrylic acid unit:ethyl acrylate unit=1:1) manufactured by Evonik Roehm GmbH, and the like. Of the aforementioned polymers, hydroxypropylmethylcellulose is preferable.

For stabilization of nano-cocrystal, the concentration of the polymer in water is preferably 0.3-2.5% (w/v), more preferably 0.3-2.0% (w/v), further preferably 0.3-1.5% (w/v).

Examples of the surfactant include sodium dodecyl sulfate, cetyltrimethylammonium bromide, polysorbate 80, sodium dioctylsulfosuccinate (alias name: dioctyl sodium sulfosuccinate) and the like. Of these, sodium dodecyl sulfate is preferable.

For stabilization of nano-cocrystal, the concentration of the surfactant in water is preferably 0.02-0.30% (w/v), more preferably 0.03-0.20% (w/v), further preferably 0.04-0.15% (w/v).

When the poorly soluble drug is a neutral organic compound, a salt thereof for improving the dissolution property cannot be formed. However, it is possible to improve the dissolution property of a neutral organic compound by forming a cocrystal thereof. Therefore, an organic compound constituting the cocrystal may be any of a neutral compound, an acidic compound, a basic compound and an ampholytic compound. Here, the ampholytic compound means a compound having both an acidic functional group and a basic functional group.

Examples of the neutral compound include carbamazepine, griseofulvin, progesterone, fenofibrate, paclitaxel and the like. Examples of the acidic compound include indomethacin, ibuprofen, naproxen, ketoprofen, mefenamic acid and the like. Examples of the basic compound include itraconazole, ketoconazole, omeprazole, cimetidine, diazepam and the like. Examples of the ampholytic compound include furosemide, sulfamethoxazole, piroxicam, meloxicam, enoxacin and the like. Of the aforementioned organic compounds, furosemide, carbamazepine and indomethacin are preferable.

Examples of the cocrystal former constituting the cocrystal include saccharin, caffeine, fumaric acid, maleic acid, tartaric acid, succinic acid, malic acid, oxalic acid, citric acid, lactic acid, glycolic acid, hippuric acid, cinnamic acid, malonic acid, adipic acid, mandelic acid, sebacic acid, ascorbic acid, glutamic acid, aspartic acid, glutaric acid, lysine, arginine, tryptophan, benzoic acid, nicotinic acid, salicylic acid, gentisic acid, orotic acid, pamoic acid, lauric acid, palmitic acid, stearic acid, urea, piperazine, hydroquinone, tyrosine, glycine, asparagine, glutamine, valine, serine, proline, alanine, methionine, histidine, threonine, leucine, isoleucine, phenylalanine, nicotinamide, acetamide, benzamide, glycol amide, 4-aminobenzoic acid, 4-hydroxybenzoic acid, benzenesulfonic acid, p-toluenesulfonic acid, imidazole, xylitol, tromethamine, and salts thereof (e.g., saccharin sodium) and the like. Of these, saccharin and caffeine are preferable.

Cocrystal can be produced, for example, from an organic compound and a cocrystal former by a known method (e.g., grinding method, slurry aging method etc.) as those described in non-patent documents 3 and 4.

In the present invention, a cocrystal having a ratio of water solubility (mg/mL) of cocrystal former/water solubility (mg/mL) of organic compound of less than $1.0 \times 10^5$ is preferably used. When the water solubility of the organic compound and that the cocrystal former differ markedly, a cocrystal obtained from these becomes unstable, and is sometimes dissociated during wet grinding. The ratio is more preferably not more than $5.0 \times 10^4$, further preferably not more than $1.0 \times 10^4$. The water solubility is a value at 25° C. and 1 atm.

For stabilization of nano-cocrystal, the concentration of nano-cocrystal in water is preferably 1-1000 mg/mL (i.e., 0.1-100% (w/v)), more preferably 5-500 mg/mL (i.e., 0.5-50% (w/v)), further preferably 10-200 mg/mL (i.e., 1.0-20% (w/v)).

Examples of an instrument used for the wet grinding include planetary mill, bead mill, attritor and the like. Of these, planetary mill and bead mill using beads as a grinding medium are preferable, and a planetary mill using beads is more preferable.

Examples of the material of the bead include zirconia, alumina, glass, steel and the like. Of these, zirconia is preferable. The diameter of the bead is preferably 0.01-5.0 mm, more preferably 0.02-1.0 mm. The amount of the beads to be used is preferably 1-40 volume %, more preferably 4-12 volume %, of the volume of the grinding chamber of planetary mill, bead mill and the like. Wet grinding while cooling the grinding chamber is preferable. The temperature of the grinding chamber during wet grinding is preferably −20° C. to 0° C., more preferably −15° C. to −5° C.

When a planetary mill is used, the rotating speed of the rotation of the grinding chamber is preferably 400-2000 rpm, more preferably 500-2000 rpm, and the rotating speed of the revolution is 400-2000 rpm, more preferably 500-2000 rpm. The amount of a suspension to be supplied to the grinding chamber of a planetary mill is preferably 1-40 volume %, more preferably 4-12 volume %, of the volume of the grinding chamber. The time of one cycle of wet grinding in a planetary mill is preferably 1-15 min, more preferably 1-5 min. In a planetary mill, wet grinding is repeated in preferably 1-10 cycles, more preferably 3-5 cycles.

When a bead mill is used, the rotating speed of the rotation axis of the bead mill is preferably 500-5000 rpm, more preferably 1000-4000 rpm. The amount of a suspension to be supplied to the grinding chamber of a bead mill is preferably 1-120 kg/time, more preferably 6-60 kg/time. A suspension may be repeatedly supplied to the grinding chamber of the bead mill until a nano-cocrystal having a desired average particle size is obtained.

A nano-cocrystal having an average particle size of not more than 300 nm may be collected by filtration from a suspension obtained by the above-mentioned production method by using a precision filtration membrane or ultra filtration membrane.

A composition containing a nano-cocrystal having an average particle size of not more than 300 nm, a polymer and a surfactant may be produced by drying a suspension obtained by the above-mentioned production method. Explanation of the nano-cocrystal, polymer and surfactant contained in the composition obtained by this method is as described above.

Examples of the dry method include spray dry, drying by heating, drying under reduced pressure and the liked. Of these, spray dry is preferable. Examples of a gas to be used for spray dry include nitrogen, air and the like. The temperature of the gas to be used for spray dry is preferably 25-120° C., more preferably 50-120° C.

The amount of the polymer in the obtained composition is preferably 1.5-250 parts by weight, more preferably 5-100 parts by weight, per 100 parts by weight of the nano-cocrystal. The amount of the surfactant in the obtained composition is preferably 0.1-30 parts by weight, more preferably 0.5-10 parts by weight, per 100 parts by weight of the nano-cocrystal.

The present invention also provides a medicament containing a suspension or composition obtained as mentioned above. The medicament may be a liquid preparation (e.g., injection etc.) or a solid preparation (e.g., granule, fine granules, capsule etc.). When a nano-cocrystal contained in the suspension can pass a sterilization filtration membrane (about 200 nm), for example, the suspension is dispersed in an injection fluid and sterilized by filtration, whereby an to injection can be produced. In addition granules can also be produced by, for example, formulating a carrier on which the suspension was sprayed.

EXAMPLES

The present invention is explained in more detail in the following by referring to Examples, which do not limit the present invention. It is also possible to carry out the present invention by making appropriate modifications within the range that can conform to the above and the following gist, all of which are encompassed in the technical scope of the present invention.

1. Abbreviation

The abbreviations used in the following Examples mean as described below.

(1) organic compound
  FSD: furosemide
  CBZ: carbamazepine
  IMC: indomethacin
(2) cocrystal former
  SAC: saccharin
  CAF: caffeine UREA: urea
ACT: acetamide
NIC: nicotinamide
(3) polymer and surfactant
HPMC: hydroxypropylmethylcellulose
SDS: sodium dodecyl sulfate
(4) others
FSD physical mixture: suspension containing FSD, HPMC and SDS
FSD-CAF physical mixture: suspension containing FSD-CAF cocrystal, HPMC and SDS
CBZ physical mixture: suspension containing CBZ, HPMC and SDS
CBZ-SAC physical mixture: suspension containing CBZ-SAC cocrystal, HPMC and SDS 2. Materials Furosemide used as an organic compound (ampholytic compound, molecular weight=330.74 g/mol, purity ≥99.0%, water solubility=0.006 mg/mL) was purchased from Tokyo Chemical Industry Co., Ltd., and anhydrous carbamazepine (neutral compound, molecular weight=236.27 g/mol, purity≥97.0%, water solubility=0.22 mg/mL) and indomethacin (acidic compound, molecular weight=357.79 g/mol, purity ≥98.0%, water solubility=0.0095 mg/mL) were purchased from Wako Pure Chemical Industries, Ltd.

Saccharin (water solubility=3.4 mg/mL), caffeine (water solubility=22 mg/mL), urea (water solubility=1,000 mg/mL), acetamide (water solubility=2,000 mg/mL) and nicotinamide (water solubility=1,000 mg/mL) used as a cocrystal former were purchased from Wako Pure Chemical Industries, Ltd.

Hydroxypropylmethylcellulose (TC-5E grade, weight average molecular weight=16,000) used as a polymer was purchased from Shin-Etsu Chemical Co., Ltd.

Sodium dodecyl sulfate used as a surfactant was purchased from Wako Pure Chemical Industries, Ltd.

All organic solvents used for the production of cocrystal were purchased from Wako Pure Chemical Industries, Ltd.

3. Production of Cocrystal (1) Production of Cocrystal Containing FSD

FSD-CAF cocrystal, FSD-UREA cocrystal, FSD-ACT cocrystal and FSD-NIC cocrystal were produced by a grinding method using a few drops of an organic solvent according to the description of non-patent document 3. To be specific, equimolar FSD and cocrystal former were weighed out in a mortar, 5-6 drops of an organic solvent (acetonitrile for FSD-CAF and FSD-ACT, acetone for FSD-NIC) were added and the mixture was ground with a pestle for 20 min. The resulting powder was collected and vacuum dried at room temperature to give a cocrystal.

(2) Production of Cocrystal Containing CBZ

CBZ-SAC cocrystal was produced by a slurry aging method. To be specific, equimolar CBZ and SAC were dispersed in acetonitrile, and the obtained slurry was stood at room temperature overnight. The obtained precipitate was collected by vacuum filtration, and vacuum dried at room temperature to give a CBZ-SAC cocrystal.

(3) Production of Cocrystal Containing IMC

IMC-SAC cocrystal was produced by a slurry aging method according to the description of non-patent document 4. To be specific, equimolar IMC and SAC were dispersed in acetonitrile, and the obtained slurry was stood at room temperature for 3 days. The obtained precipitate was collected by vacuum filtration, and vacuum dried at room temperature to give a IMC-SAC cocrystal.

4. Production of Suspension by Wet Grinding

Example 1

FSD-CAF cocrystal (water solubility of CAF/water solubility of FSD=$3.7\times10^3$) was dispersed in distilled water containing 0.5% (w/v) HPMC and 0.02% (w/v) SDS (hereinafter "blend solution"), and the dispersion was subjected to wet grinding by rotating/revolving Nano Pulverizer NP-100 (manufactured by THINKY CORPORATION, planetary mill) using zirconia beads to give a suspension containing FSD-CAF nano-cocrystal. To be specific, using vortex mixer VTX-3000L (manufactured by LMS Co., Ltd.), FSD-CAF cocrystal (100 mg) was dispersed in a blend solution (5 mL, 17 volume % relative to the volume of grinding chamber) in a grinding chamber (volume 30 mL), and the obtained suspension was poured into a grinding chamber containing zirconia beads (diameter 0.1 mm, 10 g, 8 volume % relative to the volume of grinding chamber). Wet grinding was performed by 3 repeats of a cycle including rotation and revolution each at a rotating speed of 2000 rpm for 2 min and rotation and revolution each at a rotating speed of 500 rpm for 2 min. During the wet grinding, the grinding chamber was maintained at −10° C. A mixture of zirconia beads and the suspension obtained after wet grinding was placed in a centrifugation filter/mesh chamber, rotated at 400 rpm for 1 min to separate the zirconia beads and collect the suspension (concentration FSD-CAF nano-cocrystal in water=20 mg/mL=2% (w/v)).

Example 2

In the same manner as in Example 1 except that a CBZ-SAC cocrystal (water solubility of SAC/water solubility of CBZ=$1.5\times10$) was used instead of the FSD-CAF cocrystal, a suspension of the CBZ-SAC nano-cocrystal was produced.

Example 3

In the same manner as in Example 1 except that an IMC-SAC cocrystal (water solubility of SAC/water solubility of IMC=$3.6\times10^2$) was used instead of the FSD-CAF cocrystal, a suspension of the IMC-SAC nano-cocrystal was produced.

Comparative Example 1

In the same manner as in Example 1 except that FSD was used instead of the FSD-CAF cocrystal, a suspension of the nanoized FSD was produced.

Comparative Example 2

In the same manner as in Example 1 except that an FSD-UREA cocrystal (water solubility of UREA/water solubility of FSD=$1.7\times10^5$) was used instead of the FSD-CAF cocrystal, a suspension was produced.

Comparative Example 3

In the same manner as in Example 1 except that an FSD-ACT cocrystal (water solubility of ACT/water solubility of FSD=$3.3\times10^5$) was used instead of the FSD-CAF cocrystal, a suspension was produced.

Comparative Example 4

In the same manner as in Example 1 except that an FSD-NIC cocrystal (water solubility of NIC/water solubility of FSD=$1.7\times10^5$) was used instead of the FSD-CAF cocrystal, a suspension was produced.

Comparative Example 5

In the same manner as in Example 1 except that CBZ was used instead of the FSD-CAF cocrystal, a suspension of the nanoized CBZ was produced.

Comparative Example 6

In the same manner as in Example 1 except that IMC was used instead of the FSD-CAF cocrystal, a suspension of the nanoized IMC was produced.

5. Property Evaluation
(1) Powder X-Ray Diffractometry

Figure 2:
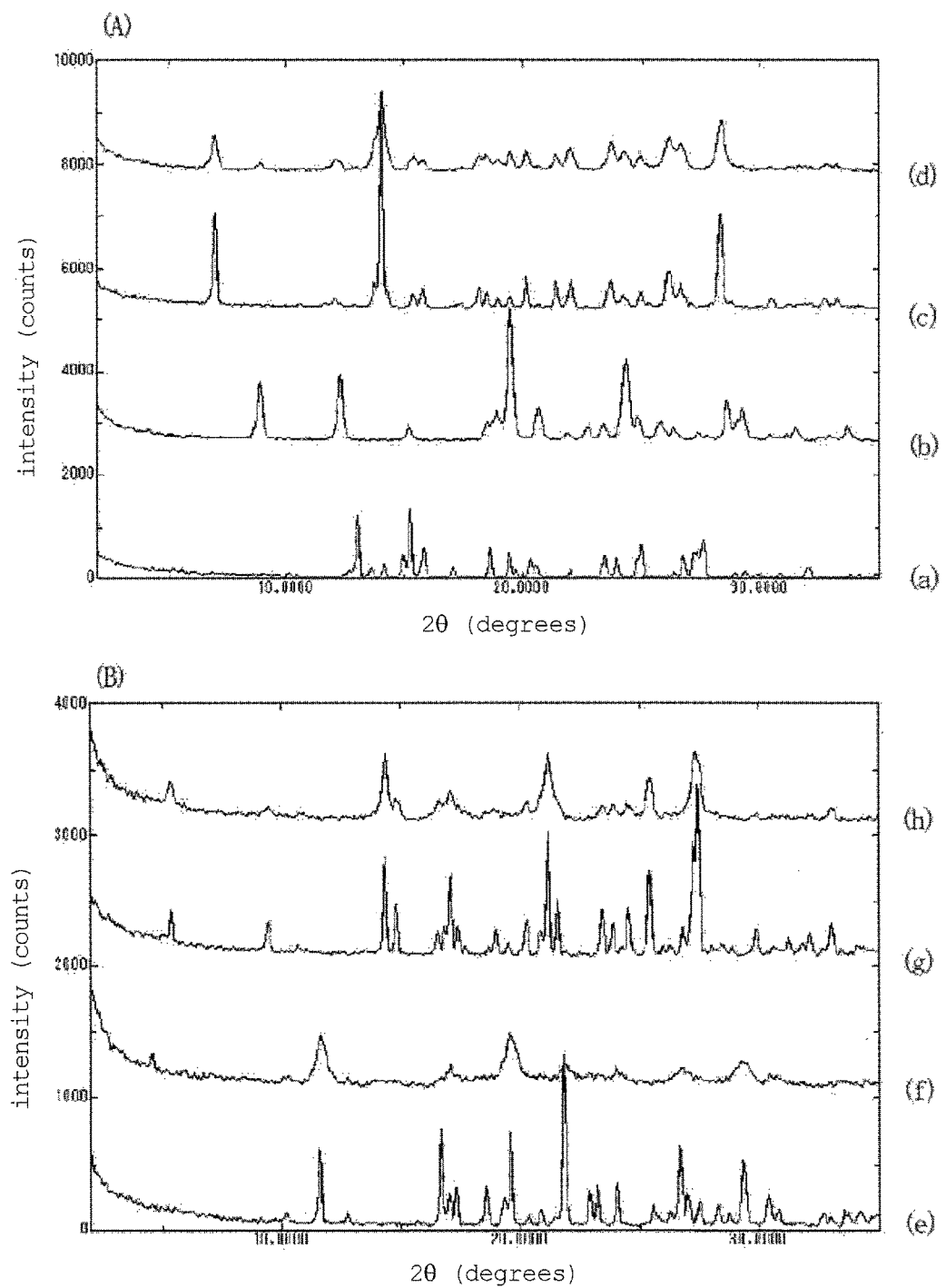
FIG. 2 shows X-ray diffraction patterns obtained by powder X-ray diffractometry, of organic compounds and cocrystals before wet grinding, and X-ray diffraction patterns of nanoized organic compounds and nano-cocrystals after wet grinding (FIG. 2(A): (a) CBZ before wet grinding, (b) nanoized CBZ after wet grinding, (c) CBZ-SAC cocrystal before wet grinding, (d) CBZ-SAC nano-cocrystal after wet grinding.

By powder X-ray diffractometry using X-ray diffractometer Ultima IV (manufactured by Rigaku Corporation) under the conditions of accelerating voltage 40 kV, tube current 50 mA and Cu Kα ray ($\lambda$=0.154 nm), X-ray diffraction patterns of FSD before wet grinding, FSD-CAF cocrystal, FSD-UREA cocrystal, FSD-ACT cocrystal, FSD-NIC cocrystal, CBZ, CBZ-SAC cocrystal, IMC and IMC-SAC cocrystal, and X-ray diffraction patterns of nanoized FSD, FSD-CAF nano-cocrystal, FSD-UREA (dissociated), FSD-ACT (dissociated), FSD-NIC (dissociated), nanoized CBZ, CBZ-SAC nano-cocrystal, nanoized IMC and IMC-SAC nano-cocrystal obtained by wet grinding in Examples 1-3 and Comparative Examples 1-6 were measured. To be specific, powder samples (about 2 mg) were placed on a silicon sample plate, and scanned between 2 and 35 degrees (2θ) at a scan speed of 6 degrees/min. Powder samples such as nanoized FSD and the like were prepared by centrifuging suspensions thereof by cooling centrifugal machine Himac CR21G (manufactured by Hitachi Koki Co., Ltd.) at 19,000 rpm for 10 min and drying same. The obtained X-ray diffraction patterns are shown in FIG. 1 and FIG. 2. In addition, from the obtained X-ray diffraction patterns by the Hermans method, crystallinity before and after wet grinding was calculated. The results are shown in Table 3-Table 5.

(2) Raman Spectrum

Figure 3:
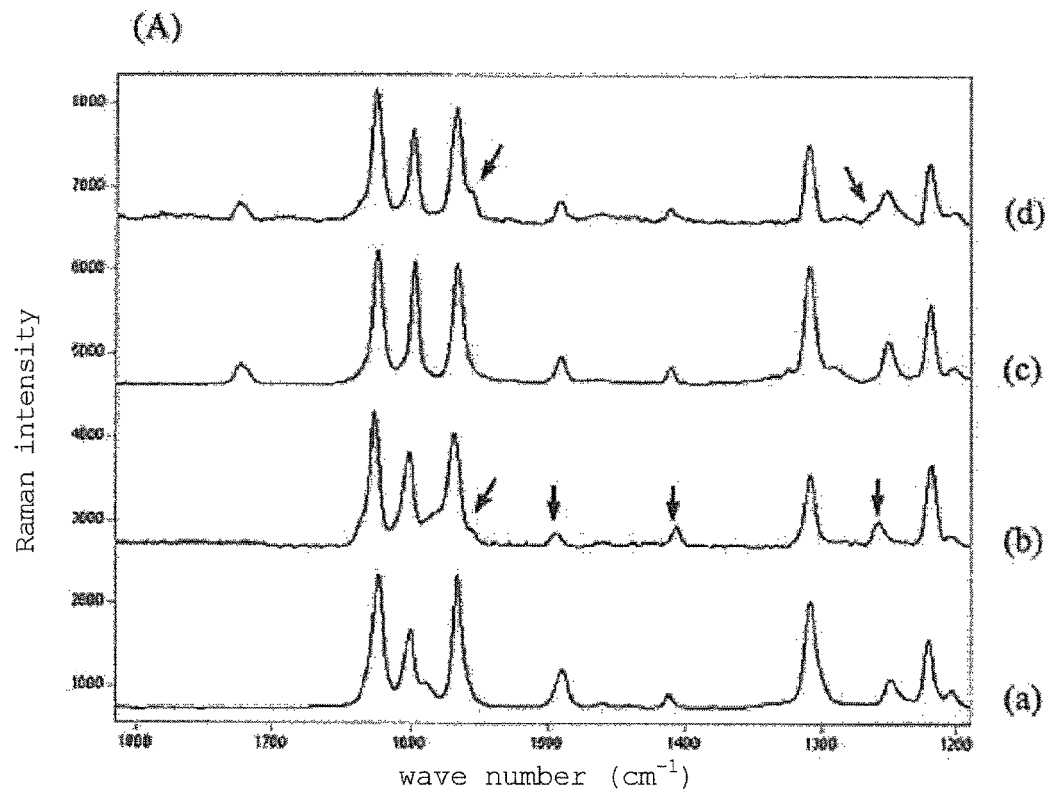
FIG. 3 shows Raman spectra of powders of organic compounds and cocrystals, and Raman spectra of suspensions of nanoized organic compounds and nano-cocrystals (FIG. 3(A): (a) a powder of CBZ, (b) a suspension of nanoized CBZ, (c) a powder of CBZ-SAC cocrystal, (d) a suspension of CBZ-SAC nano-cocrystal.
Figure 3:
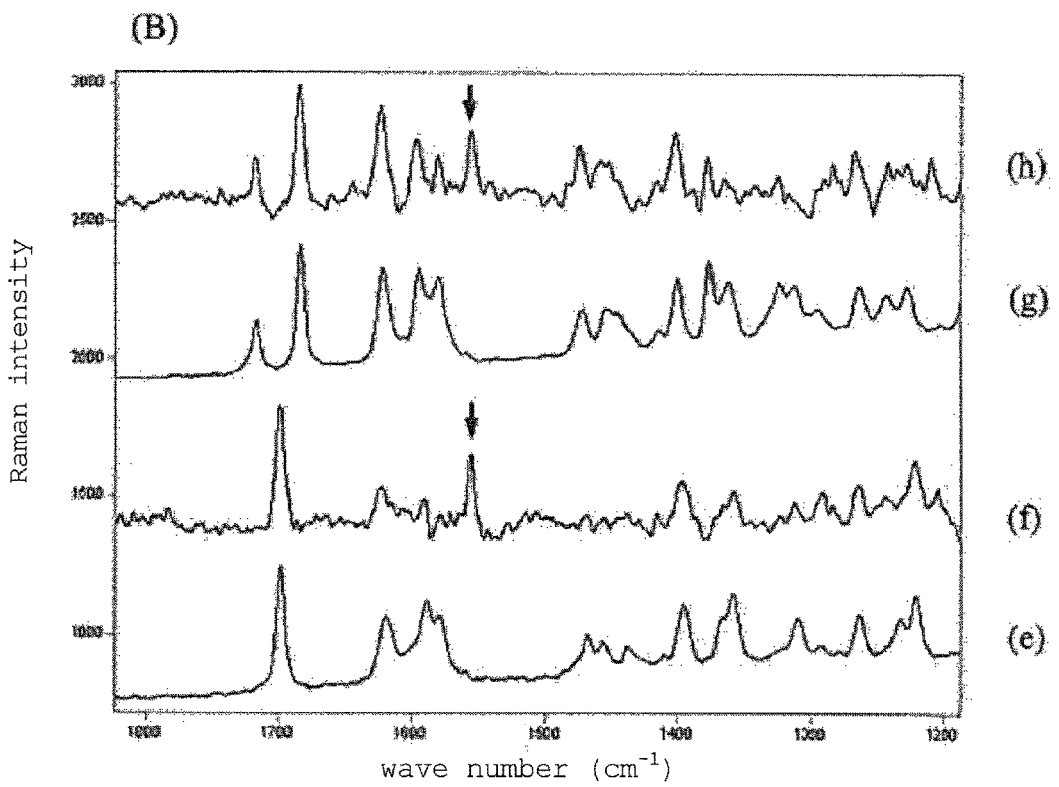

Using light-emitting diode laser (785 nm, 400 mW) as an excitation source and RXN systems (manufactured by Kaiser Optical Systems) provided with an air-cooled CCD detector, Raman spectra of the powders of CBZ, CBZ-SAC cocrystal, IMC and IMC-SAC cocrystal, and Raman spectra of suspensions of the nanoized CBZ, CBZ-SAC nano-cocrystal, nanoized IMC and IMC-SAC nano-cocrystal obtained by wet grinding in Examples 2 and 3 and Comparative Examples 5 and 6 were measured. The powders were placed on glass plates and measured, and the suspensions were placed in 2 mL quartz cells and measured. To collect the spectra, 1× objective lens provided with a probe system was used. The spectra were obtained at 4 cm$^{-1}$ spectrum width and by 10 seconds of exposure. The obtained Raman spectra are shown in FIG. 3.

(3) Average Particle Size (Dynamic Scattering Method), Polydispersity Index, Zeta Potential (Electrophoresis)

Using Malvern zetasizer nano ZS (manufactured by Malvern Instruments Ltd.), average particle size and zeta potential of the particles (nanoized FSD, FSD-CAF nano-cocrystal, nanoized CBZ, CBZ-SAC nano-cocrystal, nanoized IMC and IMC-SAC nano-cocrystal) in the suspensions obtained by wet grinding in Examples 1-3 and Comparative Examples 1, 5 and 6 were measured. In the measurement of the average particle size and zeta potential, the suspensions were each diluted 100-fold and 15-fold with distilled water. In addition, for the evaluation of the particle size distribution of the particles in the suspensions, polydispersity index (PDI) was also measured. The results are shown in Table 3-Table 5.

(4) Stability Test of Suspension

For the evaluation of the physical stability of the suspensions of nanoized FSD, FSD-CAF nano-cocrystal, nanoized CBZ, CBZ-SAC nano-cocrystal, nanoized IMC and IMC-SAC nano-cocrystal obtained by wet grinding in Examples 1-3 and Comparative Examples 1, 5 and 6, average particle size and zeta potential were measured in the same manner as above at the start of preservation, and after preservation for one month or 3 months at 5° C. or 25° C. After preservation for 3 months, Raman spectrum was measured in the same manner as above. In addition, the purity of nanoized FSD and the like were measured by HPLC under the following conditions at the start of preservation and after preservation for 3 months at 5° C. or 25° C. In the HPLC analysis, the suspension was dissolved in a mixed solvent of acetonitrile and water (volume mixing ratio 3:2), and a sample solution diluted 100-fold was used. The results are shown in Table 6-Table 11.

HPLC Conditions
  instrument: Prominence UFLC (manufactured by Shimadzu Corporation)
  detection: 230 nm
  column: YMC-Pack Pro C18, 4.6 mm i.d.×150 mm, 5 μm
  column temperature: 40° C.
  flow: 1.0 mL/min
  injection volume: 10 μL
  run time: 30 min
  mobile phase A: aqueous ammonium acetate solution (concentration: 50 mM)
  mobile phase B: acetonitrile
  gradient program: Table 1

TABLE 1

| time (min) | mobile phase B (% by volume) | |
| --- | --- | --- |
| | (1) | (2) |
| 0 | 35 | 30 |
| 10 | 35 | 30 |
| 15 | 85 | 80 |
| 20 | 85 | 80 |
| 20.1 | 35 | 30 |
| 30 | 35 | 30 |

(1) suspension of CBZ, IMC or cocrystal containing these
(2) suspension of FSD or cocrystal containing FSD (5) Dissolution Test In the Japanese Pharmacopoeia, Paddle Method, by using 250 mL of the first fluid (pH=1.2) of the Japanese Pharmacopoeia dissolution test at 37° C., a dissolution test was performed using the above-mentioned suspension and setting the paddle rotating speed of a dissolution test apparatus NTR 6100A (manufactured by TOYAMA SANGYO CO., LTD.) to 50 rpm. The eluted sample was collected at a given time point, filtered through a 0.02 μm polyethylene membrane filter (manufactured by Entegris Inc.), and the filtrate was measured by HPLC under the same conditions as the above-mentioned (4), and the dissolution concentrations of nanoized FSD, FSD-CAF nano-cocrystal, nanoized CBZ and CBZ-SAC nano-cocrystal obtained by wet grinding in Examples 1 and 2 and Comparative Examples 1 and 5 were measured. The dissolution test was performed 3 times.

Using a suspension containing FSD, HPMC and SDS (FSD physical mixture) produced by adjusting the concentration to be the same as that of the above-mentioned suspension, and mixing respective components in a vortex mixer, a suspension containing FSD-CAF cocrystal, HPMC and SDS (FSD-CAF physical mixture), a suspension containing CBZ, HPMC and SDS (CBZ physical mixture), and a suspension containing CBZ-SAC cocrystal, HPMC and SDS (CBZ-SAC physical mixture), the dissolution concentrations of FSD, FSD-CAF cocrystal, CBZ and CBZ-SAC cocrystal were measured in the same manner as above.

Figure 4:
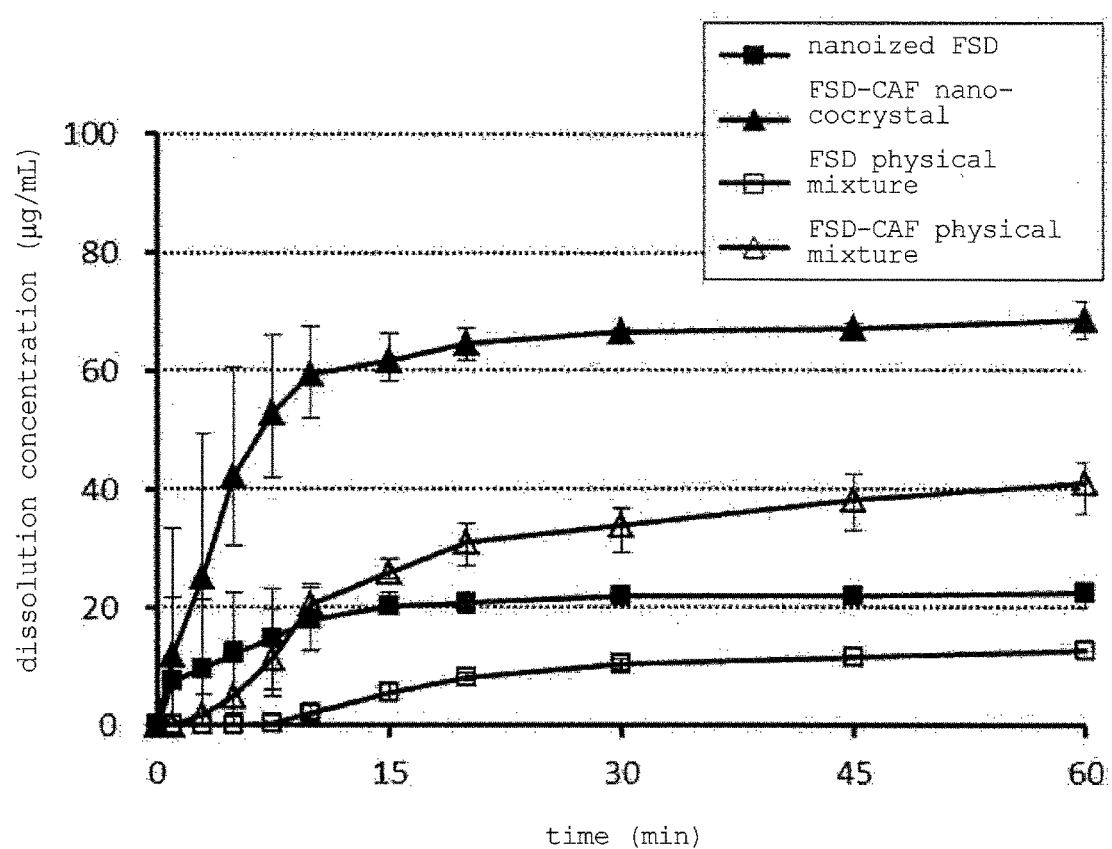
FIG. 4 is a graph showing the relation of dissolution concentration-time in the first fluid (pH=1.2) of the Japanese Pharmacopoeia dissolution test using a suspension of nanoized FSD, a suspension of FSD-CAF nano-cocrystal, an FSD physical mixture, or an FSD-CAF physical mixture. The abbreviations mean as described in the Examples.
Figure 5:
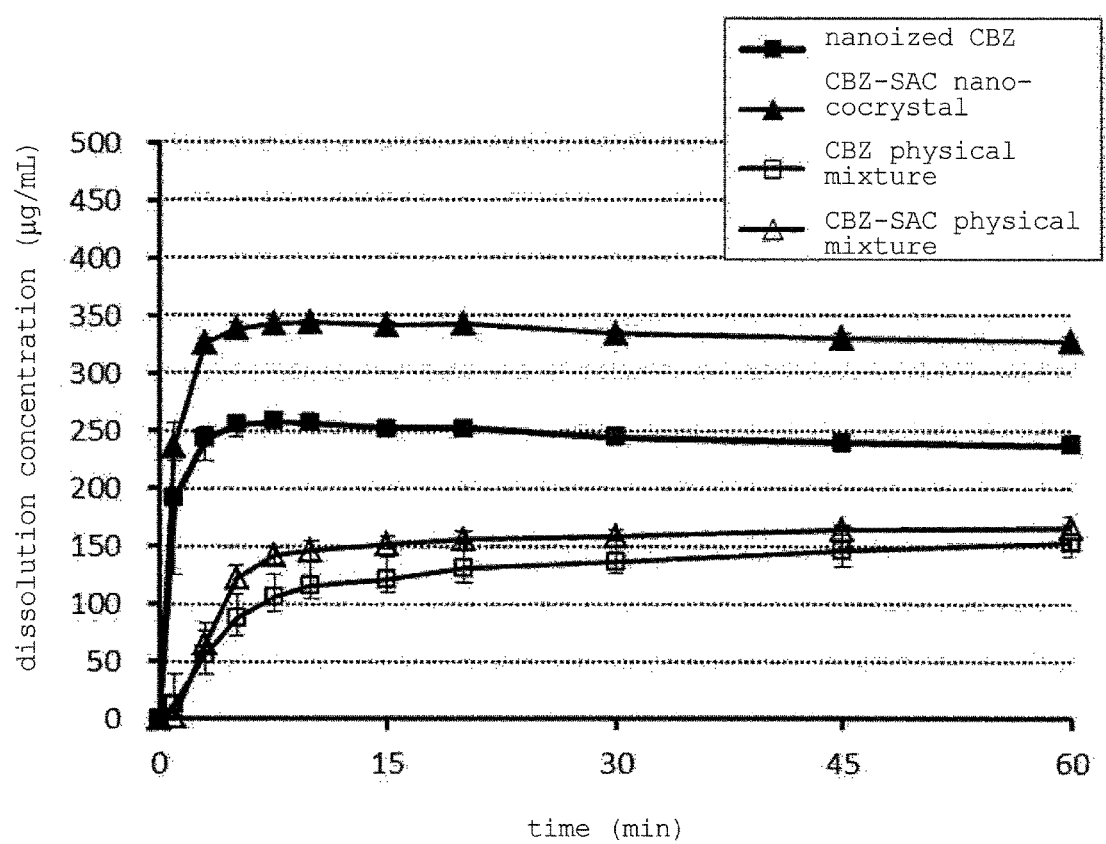
FIG. 5 is a graph showing the relation of dissolution concentration-time in the first fluid (pH=1.2) of the Japanese Pharmacopoeia dissolution test using a suspension of nanoized CBZ, a suspension of CBZ-SAC nano-cocrystal, a CBZ physical mixture, or a suspension of a CBZ-SAC physical mixture. The abbreviations mean as described in the Examples.

The results (mean) are shown in FIG. 4 and FIG. 5.

(6) Pharmacokinetics Test Using Rat

Figure 6:
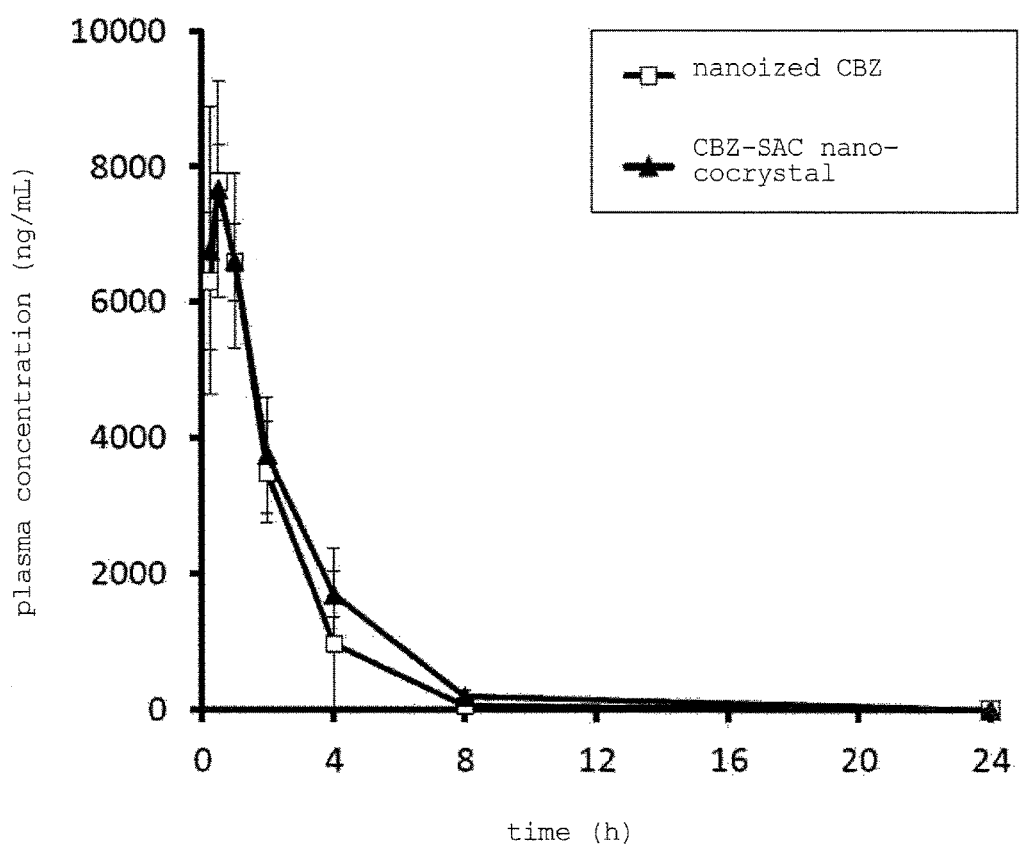
FIG. 6 is a graph showing CBZ concentration-time in the plasma of a diluted suspension of nanoized CBZ and CBZ-SAC nano-cocrystal obtained by wet grinding (concentration: 5 mg/mL). The abbreviations mean as described in the Examples.

The concentration of a suspension of CBZ-SAC nanococrystal obtained by wet grinding in Example 2 and a suspension of nanoized CBZ obtained by wet grinding in Comparative Example 5 was diluted with 5 mg/mL with distilled water. The obtained suspensions were each administered orally to Crl: CD(SD)IGS rats (8-week-old, male, CHARLES RIVER LABORATORIES JAPAN, INC.) in a fasting state. The dose was set to 25 mg/5 mL/kg as free CBZ, and each suspension was administered 3 times. Blood samples were collected at 15 and 30 min, and 1, 2, 4, 8 and 24 hr after administration, and centrifuged to give plasma. The concentration of CBZ in the obtained plasma was measured by LC/MS/MS under the following conditions. The results (mean) are shown in FIG. 6. From the obtained concentration curve, the maximum blood concentration ($C_{max}$) and maximum blood concentration reaching time ($T_{max}$) of the drug were measured. In addition, mean residence time (MRT) was calculated by the moment analysis, and 0-24 hr area under the blood concentration-time curve ($AUC_{0-24h}$) of the drug was calculated by the trapezoidal method.

LC/MS/MS Measurement Conditions
  instrument: Prominence UFLC (manufactured by Shimadzu Corporation)
  detection: API4000-3 (manufactured by AB Sciex Pte. Ltd.)
  ionization mode: turbo ion spray
  ion polarity mode: positive
  turbo probe temperature: 550° C.
  column: CAPCELL CORE C18 (2.1 mm×50 mm, 2.7 μm)
  column temperature: 50° C.
  flow: 0.5 mL/min
  injection volume: 1 μL
  run time: 7 min
  mobile phase A: aqueous solution of ammonium formate (10 mmol/L) and formic acid (0.2% by volume)
  mobile phase B: acetonitrile solution of formic acid (0.2% by volume)
  gradient program: Table 2

TABLE 2

| time (min) | mobile phase B (% by volume) |
| --- | --- |
| 0 | 20 |
| 0.5 | 20 |
| 3.0 | 80 |
| 3.1 | 95 |
| 5.0 | 95 |
| 5.1 | 20 |
| 7.0 | 20 |

To the aforementioned rats were intravenously administered a CBZ solution dissolved in a dimethylacetamide/1,3-butanediol mixed solvent (volume mixing ratio of dimethylacetamide:1,3-butanediol=1:1) at a dose of 3 mg/1 mL/kg. The intravenous administration was performed 3 times. Blood samples were collected at 5, 10, 15 and 30 min, and 1, 2, 4, 8 and 24 hr after the intravenous administration, and the concentration of CBZ in the plasma was measured in the same manner as in oral administration. $AUC_{0-24h}$ was calculated from the obtained concentration curve. Bioavailability (BA) was calculated from the mean of $AUC_{0-24h}$ after oral administration and intravenous administration and by the following formula. The results are shown in Table 12.

BA (%)=100×($AUC_{p.o.}$×$Dose_{i.v.}$)/($AUC_{i.v.}$×$Dose_{p.o.}$)

wherein $AUC_{p.o.}$ is AUC in oral administration, $AUC_{i.v.}$ is AUC in intravenous administration, $Dose_{p.o.}$ is oral dose, and $Dose_{i.v.}$ is intravenous dose.

TABLE 3

| | | FSD | FSD-CAF |
| --- | --- | --- | --- |
| average particle size (nm) | | 165 | 194 |
| PDI | | 0.180 | 0.229 |
| zeta potential (mV) | | −28.7 | −26.2 |
| crystallinity | before wet grinding | 85 | 85 |
| (%) | after wet grinding | 61 | 53 |

TABLE 4

| | | CBZ | CBZ-SAC |
| --- | --- | --- | --- |
| average particle size (nm) | | 225 | 270 |
| PDI | | 0.145 | 0.165 |
| zeta potential (mV) | | −24.4 | −4.84 |
| crystallinity | before wet grinding | 88 | 86 |
| (%) | after wet grinding | 71 | 62 |

TABLE 5

| | | IMC | IMC-SAC |
| --- | --- | --- | --- |
| average particle size (nm) | | 167 | 177 |
| PDI | | 0.146 | 0.135 |
| zeta potential (mV) | | −29.7 | −22.5 |
| crystallinity | before wet grinding | 81 | 87 |
| (%) | after wet grinding | 62 | 60 |

TABLE 6

Stability of nanoized FSD

| | start of preservation | 5° C. one month | 5° C. 3 months | 25° C. one month | 25° C. 3 months |
| --- | --- | --- | --- | --- | --- |
| average particle size (nm) | 164 | 160 | 168 | 170 | 164 |
| PDI | 0.180 | 0.202 | 0.187 | 0.198 | 0.229 |
| zeta potential (mV) | −28.7 | −25.3 | −24.4 | −26.7 | −28.1 |
| purity (%) | 99.8 | — | 99.6 | — | 99.5 |

TABLE 7

Stability of FSD-CAF nano-cocrystal

| | start of preservation | 5° C. one month | 5° C. 3 months | 25° C. one month | 25° C. 3 months |
| --- | --- | --- | --- | --- | --- |
| average particle size (nm) | 194 | 194 | 194 | 200 | 195 |
| PDI | 0.229 | 0.216 | 0.215 | 0.214 | 0.203 |

TABLE 7-continued

Stability of FSD-CAF nano-cocrystal

|  | start of preservation | 5° C. one month | 5° C. 3 months | 25° C. one month | 25° C. 3 months |
|---|---|---|---|---|---|
| zeta potential (mV) | −26.2 | −21.3 | −20.8 | −24.7 | −21.8 |
| purity (%) | 99.9 | — | 99.7 | — | 99.6 |

TABLE 8

Stability of nanoized CBZ

|  | start of preservation | 5° C. one month | 5° C. 3 months | 25° C. one month | 25° C. 3 months |
|---|---|---|---|---|---|
| average particle size (nm) | 225 | 223 | 223 | 230 | 237 |
| PDI | 0.145 | 0.161 | 0.166 | 0.150 | 0.134 |
| zeta potential (mV) | −24.4 | −25.4 | −24.5 | −24.8 | −22.6 |
| purity (%) | 99.8 | — | 99.8 | — | 99.8 |

TABLE 9

Stability of CBZ-SAC nano-cocrystal

|  | start of preservation | 5° C. one month | 5° C. 3 months | 25° C. one month | 25° C. 3 months |
|---|---|---|---|---|---|
| average particle size (nm) | 270 | 265 | 296 | 298 | 341 |
| PDI | 0.165 | 0.179 | 0.229 | 0.143 | 0.186 |
| zeta potential (mV) | −4.84 | −5.44 | −3.05 | −4.36 | −3.62 |
| purity (%) | 99.9 | — | 99.8 | — | 99.9 |

TABLE 10

Stability of nanoized IMC

|  | start of preservation | 5° C. one month | 5° C. 3 months | 25° C. one month | 25° C. 3 months |
|---|---|---|---|---|---|
| average particle size (nm) | 167 | 150 | 149 | 151 | 149 |
| PDI | 0.146 | 0.160 | 0.137 | 0.140 | 0.118 |
| zeta potential (mV) | −29.7 | −33.1 | −31.3 | −32.4 | −35.8 |
| purity (%) | 99.8 | — | 99.4 | — | 99.1 |

TABLE 11

Stability of IMC-SAC nano-cocrystal

|  | start of preservation | 5° C. one month | 5° C. 3 months | 25° C. one month | 25° C. 3 months |
|---|---|---|---|---|---|
| average particle size (nm) | 177 | 189 | 191 | 186 | 191 |
| PDI | 0.135 | 0.196 | 0.179 | 0.163 | 0.184 |
| zeta potential (mV) | −22.5 | −22.1 | −18.8 | −23.0 | −20.2 |
| purity (%) | 99.8 | — | 99.6 | — | 99.6 |

TABLE 12

Pharmacokinetics test using rat

|  | nanoized CBZ | CBZ-SAC nano-cocrystal |
|---|---|---|
| $C_{max}$ (ng/mL) | 7773.0 ± 1592.4 | 7843.4 ± 289.9 |
| $T_{max}$ (time) | 0.50 ± 0.00 | 0.42 ± 0.14 |
| $AUC_{0-24\,h}$ (ng · time/mL) | 18208.2 ± 4484.2 | 22201.4 ± 7796.7 |
| MRT (time) | 1.85 ± 0.15 | 2.25 ± 0.79 |
| BA (%) | 78.7 ± 25.5 | 96.0 ± 39.3 |

As shown in FIG. 1, while FSD and FSD-CAF cocrystal did not show a marked difference in the diffraction pattern before and after the wet grinding (FIG. 1 (a)-(d)), the diffraction pattern of powders obtained after wet grinding of FSD-UREA cocrystal, FSD-ACT cocrystal and FSD-NIC cocrystal showed a diffraction pattern of pure FSD ((FIG. 1 (f), (h) and (j))). From these results, it is clear that the FSD-UREA cocrystal, FSD-ACT cocrystal and FSD-NIC cocrystal were dissociated by wet grinding. Dissociation of FSD-UREA cocrystal, FSD-ACT cocrystal and FSD-NIC cocrystal by wet grinding is assumed to be attributable to the marked difference in the water solubility of FSD as an organic compound and UREA, ACT or NIC as a cocrystal former (water solubility of UREA/water solubility of FSD=$1.7\times10^5$, water solubility of ACT/water solubility of FSD=$3.3\times10^5$, water solubility of NIC/water solubility of FSD=$1.7\times10^5$), which caused instability of the obtained cocrystals. As shown in Table 3, moreover, a suspension of FSD-CAF nano-cocrystal having an average particle size of less than 200 nm and low PDI can be obtained by wet grinding FSD-CAF cocrystal using a polymer (HPMC) and a surfactant (SDS) in combination.

From the diffraction pattern shown in FIG. 2(A), while formation of CBZ dihydrate could be confirmed by wet grinding of anhydrous CBZ (FIG. 2(A)(b)), formation of hydrate was not confirmed by wet grinding of CBZ-SAC cocrystal (FIG. 2(A)(d)). Thus, hydration during wet grinding can be prevented by first cocrystallizing CBZ and then wet grinding same, rather than simply wet grinding the organic compound. As shown in Table 4, moreover, a suspension of CBZ-SAC nano-cocrystal having an average particle size of less than 300 nm and low PDI can be obtained by wet grinding CBZ-SAC cocrystal using a polymer (HPMC) and a surfactant (SDS) in combination.

As shown in FIG. 2(B) and Table 5, a suspension of IMC-SAC nano-cocrystal having an average particle size of less than 200 nm and low PDI can be obtained by wet grinding IMC-SAC cocrystal using a polymer (HPMC) and a surfactant (SDS) in combination.

As shown in Table 7, Table 9 and Table 11, the average particle size of the FSD-CAF nano-cocrystal, CBZ-SAC nano-cocrystal and IMC-SAC nano-cocrystal in suspension was maintained at a sufficiently low level after one month preservation. Note that preservation of a suspension for a long term exceeding one month is not performed in industrial working.

As shown in FIG. 4, the FSD-CAF nano-cocrystal obtained by first performing cocrystallization and then wet grinding was superior in the dissolution property in the first fluid of the Japanese Pharmacopoeia dissolution test than the FSD-CAF cocrystal obtained by cocrystallization (FSD-CAF physical mixture) and the nanoized FSD obtained by wet grinding.

As shown in FIG. 5, moreover, the CBZ-SAC nano-cocrystal obtained by first performing cocrystallization and then wet grinding was superior in the dissolution property in the first fluid of the Japanese Pharmacopoeia dissolution test than the CBZ-SAC cocrystal obtained by cocrystallization (CBZ-SAC physical mixture) and the nanoized CBZ obtained by wet grinding.

As shown above, the dissolution property of an organic compound can be further improved by a combination of cocrystallization and wet grinding, rather than simple cocrystallization or wet grinding.

As shown in Table 12, CBZ-SAC nano-cocrystal showed $AUC_{0-24h}$ which was 1.2-fold that of nanoized CBZ. While bioavailability (BA) of nanoized CBZ was 78.7%, that of the CBZ-SAC nano-cocrystal was 96.0%. As shown above, the CBZ-SAC nano-cocrystal obtained by first cocrystallizing CBZ, and then subjecting same to wet grinding was superior in the absorbability as compared to nanoized CBZ obtained by simple wet grinding.

(7) Solid $^{13}C$ NMR Measurement

Figure 7:
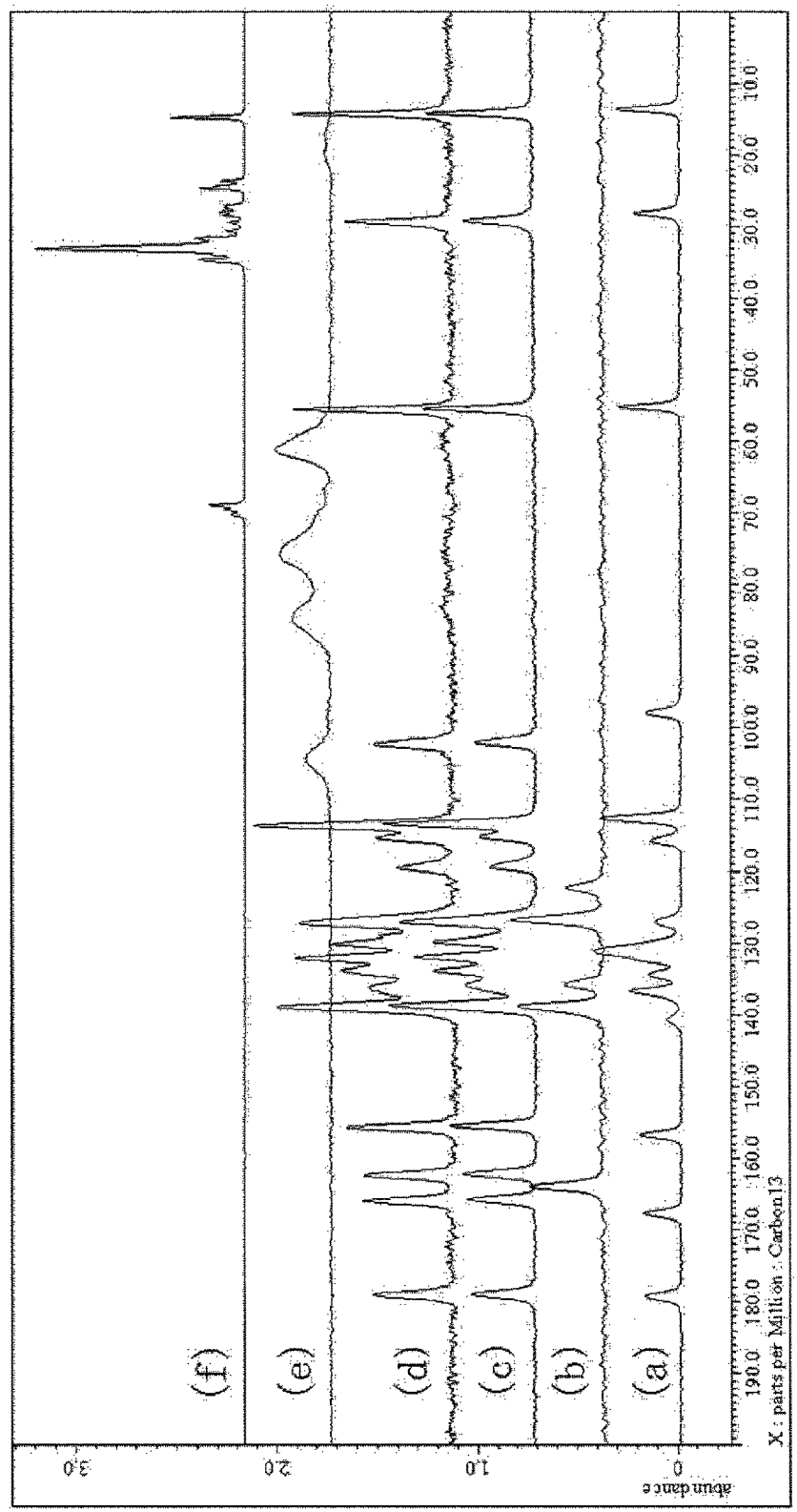
FIG. 7 shows solid $^{13}$C NMR spectra of a suspension of IMC-SAC nano-cocrystal ((a) a powder of IMC, (b) a powder of SAC, (c) a powder of IMC-SAC cocrystal before wet grinding, (d) a suspension of IMC-SAC nano-cocrystal after wet grinding, (e) a powder of HPMC, (f) a powder of SDS). The abbreviations mean as described in the Examples.

In the same manner as in Example 3, the solid $^{13}C$ NMR of a suspension of IMC-SAC nano-cocrystal produced by wet grinding in distilled water containing 0.5% (w/v) HPMC and 0.02% (w/v) SDS was measured using NMR apparatus JNM-ECX500II (11.7T) manufactured by JEOL RESONANCE. Similarly, the solid $^{13}C$ NMR of a powder of IMC, a powder of SAC, a powder of IMC-SAC cocrystal before wet grinding, a powder of HPMC and a powder of SDS was measured. To be specific, the solid $^{13}C$ NMR of the aforementioned samples was measured with 3.2 mmHX MAS probe at room temperature by the cross polarization/magic angle rotation (CP/MAS) method at 6 KHz sample rotating speed, and using hexamethylbenzene (—$CH_3$: 17.17 ppm) as an external standard substance. The obtained solid $^{13}C$ NMR spectra are shown in FIG. 7.

Figure 8:
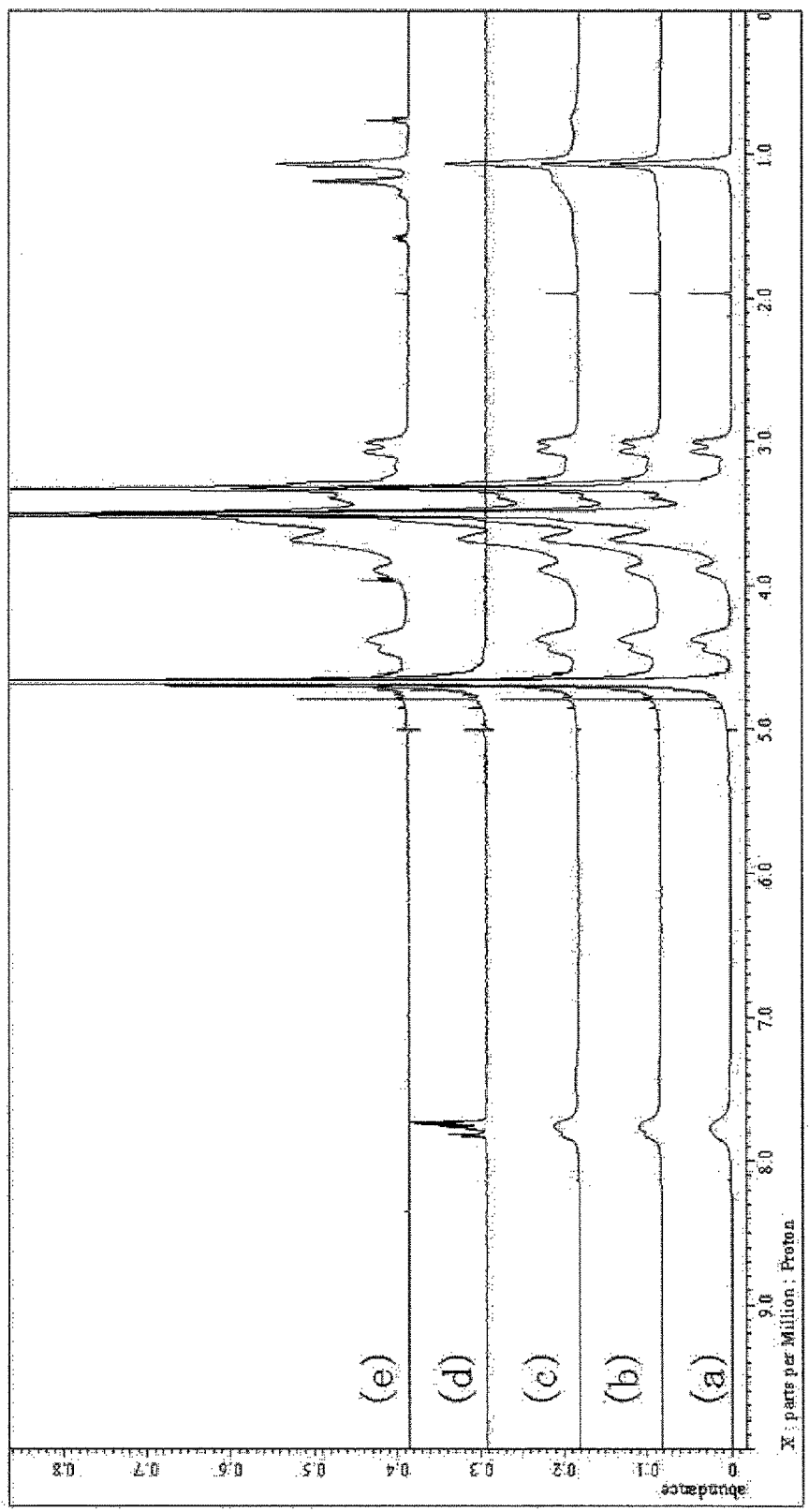
FIG. 8 shows solution $^{1}$H spectra of a suspension of CBZ-SAC nano-cocrystal and the like ((a) a suspension of CBZ-SAC nano-cocrystal (1% (w/v) HPMC and 0.02% (w/v) SDS), (b) a suspension of CBZ-SAC nano-cocrystal (1% (w/v) HPMC and 0.05% (w/v) SDS), (c) a suspension of CBZ-SAC nano-cocrystal (1% (w/v) HPMC and 0.12% (w/v) SDS), (d) a deuterium oxide solution of SAC, (e) a deuterium oxide solution containing 0.5% (w/v) HPMC and 0.02% (w/v) SDS). The abbreviations mean as described in the Examples.

(8) Solution $^1H$ NMR Measurement $^1H$ NMR of a suspension of CBZ-SAC nano-cocrystal produced by wet grinding in the same manner as in the below-mentioned Example 7 (1% (w/v) HPMC and 0.02% (w/v) SDS), Example 8 (1% (w/v) HPMC and 0.05% (w/v) SDS) and Example 10 (1% (w/v) HPMC and 0.12% (w/v) SDS) except that deuterium oxide ($D_2O$) was used instead of distilled water was measured by NMR apparatus JNM-ECX500II (11.7T) manufactured by JEOL RESONANCE. Similarly, $^1H$ NMR of a deuterium oxide solution of SAC and a deuterium oxide solution containing 0.5% (w/v) HPMC and 0.02% (w/v) SDS was measured. To be specific, $^1H$ NMR of the aforementioned samples was measured with 5 mmAT/FG probe at 25° C., sample rotating speed 15 Hz, wherein the chemical shift standard was the peak (4.67 ppm) of HDO in deuterium oxide as a measurement solvent. The obtained $^1H$ NMR spectra are shown in FIG. 8.

6. Study of Concentration of Polymer and Surfactant in Wet Grinding

Examples 4-14 and Comparative Examples 7-10

A suspension of CBZ-SAC nano-cocrystal was produced by wet grinding in the same manner as in Example 2 except that the concentration of a polymer (HPMC) and a surfactant (SDS) in water was changed as shown in Table 13. The average particle size and PDI of the CBZ-SAC nano-cocrystal in the obtained suspension were measured in the same manner as above. The results are shown in Table 13.

TABLE 13

| | | | CBZ-SAC nano-cocrystal | |
|---|---|---|---|---|
| | HPMC (%(w/v)) | SDS (%(w/v)) | average particle size (nm) | PDI |
| Comp. Ex. 7 | 0.2 | — | 2171 | — |
| Comp. Ex. 8 | 1 | — | 317.6 | 0.169 |
| Comp. Ex. 9 | — | 0.01 | NG | — |
| Comp. Ex. 10 | — | 0.05 | NG | — |
| Ex. 4 | 0.3 | 0.05 | 283.9 | 0.199 |
| Ex. 5 | 0.3 | 0.08 | 215.8 | 0.191 |
| Ex. 6 | 0.3 | 0.12 | 208.5 | 0.17 |
| Ex. 7 | 1 | 0.02 | 296.6 | 0.152 |
| Ex. 8 | 1 | 0.05 | 237.2 | 0.149 |
| Ex. 9 | 1 | 0.08 | 220.1 | 0.133 |
| Ex. 10 | 1 | 0.12 | 227.6 | 0.195 |
| Ex. 11 | 1.5 | 0.02 | 260.8 | 0.151 |
| Ex. 12 | 1.5 | 0.05 | 234.1 | 0.193 |
| Ex. 13 | 1.5 | 0.08 | 229.2 | 0.153 |
| Ex. 14 | 1.5 | 0.12 | 232 | 0.171 |

NG: Average particle size was too large to measure.

As shown in Table 13, in Comparative Examples 7-10 using only one of the polymer (HPMC) and the surfactant (SDS), a suspension containing CBZ-SAC nano-cocrystal having an average particle size of not more than 300 nm could not be produced.

7. Drying and Resuspending of Nano-Cocrystal Suspension

To a suspension of IMC-SAC nano-cocrystal produced in the same manner as in Example 3 was added 2.0% (w/v) d-mannitol as an additive, and the average particle size and PDI of the IMC-SAC nano-cocrystal in the obtained suspension were measured in the same manner as above. Then, the aforementioned suspension was spray dried by a spray dry method (pump speed 1, spray speed 25%, temperature 120° C., and pressure 35 mPa, under air stream) using nanospray dryer B-90 (manufactured by BUCHI). After drying, the obtained dry powder was collected, resuspended in distilled water, and the average particle size and PDI of the IMC-SAC nano-cocrystal in the obtained suspension were measured in the same manner as above. The results thereof are shown in Table 14.

TABLE 14

| | suspension of IMC-SAC nano-cocrystal before drying | suspension of IMC-SAC nano-cocrystal after drying and resuspending |
|---|---|---|
| average particle size (nm) | 173 | 182 |
| PDI | 0.193 | 0.188 |

As shown in Table 14, a composition containing a nano-cocrystal having an average particle size of not more than 300 nm, a polymer and a surfactant could be obtained by drying a suspension of nano-cocrystal by a spray dry method and the like.

INDUSTRIAL APPLICABILITY

According to the production method of the present invention, a nano-cocrystal constituted of an organic compound and a cocrystal former, and having superior dissolution property can be obtained. Therefore, the present invention is useful for improving the dissolution property of an organic compound, particularly for improving the dissolution property of a poorly soluble drug for the development of a pharmaceutical product.

This application is based on a patent application No. 2015-040647 filed in Japan, the contents of which are incorporated in full herein.

The invention claimed is:

1. A method of producing a suspension comprising a nano-cocrystal having an average particle size of not more than 300 nm, a polymer having a weight average molecular weight of not less than 3,000, a surfactant having a weight average molecular weight of less than 3,000, and water, the method comprising wet grinding a cocrystal in water containing the polymer and the surfactant, wherein the cocrystal is constituted of an organic compound and a cocrystal former, wherein the cocrystal is not dissociated by the wet grinding, and wherein the polymer has a concentration of 0.3-2.5%(w/v) and the surfactant has a concentration of 0.02-0.30% (w/v), each in water.

2. The method according to claim 1, wherein a ratio of water solubility (mg/mL) of the cocrystal former/water solubility (mg/mL) of the organic compound is less than $1.0 \times 10^5$.

3. The method according to claim 1, wherein the polymer is at least one selected from the group consisting of hydroxypropylmethylcellulose, hydroxypropylcellulose, polyvinylpyrrolidone, poly(vinyl alcohol), polyethylene glycol, methacrylic acid copolymer and Poloxamer 407.

4. The method according to claim 1, wherein the surfactant is at least one selected from the group consisting of sodium dodecyl sulfate, cetyltrimethylammonium bromide, polysorbate 80, and sodium dioctylsulfosuccinate.

* * * * *

UNITED STATES PATENT AND TRADEMARK OFFICE
CERTIFICATE OF CORRECTION

PATENT NO.       : 10,226,426 B2  
APPLICATION NO.  : 15/554688  
DATED            : March 12, 2019  
INVENTOR(S)      : Masatoshi Karashima et al.

Page 1 of 1

It is certified that error appears in the above-identified patent and that said Letters Patent is hereby corrected as shown below:

In the Claims

In Column 21, Line 20, Claim 2 replace "$1.0\times^{105}$" with -- $1.0\times10^5$ --.

Signed and Sealed this  
Third Day of September, 2019

Andrei Iancu  
*Director of the United States Patent and Trademark Office*